United States Patent
Masini et al.

(10) Patent No.: US 11,974,924 B2
(45) Date of Patent: *May 7, 2024

(54) MODULAR PATELLA TRIALS

(71) Applicant: Howmedica Osteonics Corp., Mahwah, NJ (US)

(72) Inventors: Michael Masini, Ann Arbor, MI (US); Mohamed Soliman, Fair Lawn, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 155 days.

This patent is subject to a terminal disclaimer.

(21) Appl. No.: 17/237,667

(22) Filed: Apr. 22, 2021

(65) Prior Publication Data

US 2021/0307917 A1    Oct. 7, 2021

Related U.S. Application Data

(63) Continuation of application No. 16/157,344, filed on Oct. 11, 2018, now Pat. No. 11,013,606, which is a (Continued)

(51) Int. Cl.
*A61F 2/38* (2006.01)
*A61F 2/30* (2006.01)
*A61F 2/46* (2006.01)

(52) U.S. Cl.
CPC .......... *A61F 2/3877* (2013.01); *A61F 2/4684* (2013.01); *A61F 2002/30331* (2013.01); (Continued)

(58) Field of Classification Search
CPC ...... A61F 2/3877; A61F 2/461; A61F 2/4684; A61F 2002/30504; A61F 2002/30611; (Continued)

(56) References Cited

U.S. PATENT DOCUMENTS

| 4,731,086 A | 3/1988 | Whiteside et al. |
| 4,936,847 A | 6/1990 | Manginelli |
| (Continued) | | |

FOREIGN PATENT DOCUMENTS

WO    2004093747 A1    11/2004

OTHER PUBLICATIONS

Habermann et al., "A Multicenter Review of Patellar Complications Using a Modem Design Total Knee System", About Joints, Mar. 2008.

(Continued)

*Primary Examiner* — Christie Bahena
(74) *Attorney, Agent, or Firm* — Lerner David LLP

(57) ABSTRACT

A modular patella trial system and method is provided. A modular patella trial includes an articular element and at least one sizing element. The articular element has a length, a width, and a thickness. The articular element has a posterior and anterior surfaces separated by their thickness. The anterior surface has protrusions extending outwardly. Any of the sizing elements have a length, width, and thickness. Any such sizing elements have posterior and anterior surfaces separated by their thickness. At least one aperture extends through the posterior and anterior surfaces of the sizing elements. Such apertures are capable of receiving a corresponding protrusion of the articular element. The modular patella trial has a thickness substantially equal to the total of the thicknesses of the articular element and the sizing elements used in conjunction with the articular element.

20 Claims, 14 Drawing Sheets

FIG. 13A

Related U.S. Application Data continuation of application No. 14/208,586, filed on Mar. 13, 2014, now Pat. No. 10,130,480.

(60) Provisional application No. 61/780,641, filed on Mar. 13, 2013.

(52) U.S. Cl.
CPC ............... *A61F 2002/30367* (2013.01); *A61F 2002/30616* (2013.01); *A61F 2002/30878* (2013.01)

(58) Field of Classification Search
CPC .. A61F 2002/30614; A61F 2002/30616; A61F 2002/3881
See application file for complete search history.

(56) References Cited

U.S. PATENT DOCUMENTS

| | | | |
|---|---|---|---|
| 4,944,757 A | 7/1990 | Martinez et al. |
| 4,950,298 A | 8/1990 | Gustilo et al. |
| 5,019,103 A | 5/1991 | Van Zile et al. |
| 5,024,670 A | 6/1991 | Smith et al. |
| 5,047,058 A | 9/1991 | Roberts et al. |
| 5,062,852 A | 11/1991 | Dorr et al. |
| 5,080,675 A | 1/1992 | Lawes et al. |
| 5,152,797 A | 10/1992 | Luckman et al. |
| 5,358,530 A | 10/1994 | Hodorek |
| 5,370,693 A | 12/1994 | Kelman et al. |
| 5,458,637 A | 10/1995 | Hayes |
| 5,549,685 A | 8/1996 | Hayes |
| 5,571,194 A | 11/1996 | Gabriel |
| 5,702,464 A | 12/1997 | Lackey et al. |
| 5,766,255 A | 6/1998 | Slamin et al. |
| 5,776,201 A | 7/1998 | Colleran et al. |
| 5,910,171 A | 6/1999 | Kummer et al. |
| 5,984,969 A | 11/1999 | Matthews et al. |
| 6,074,424 A | 6/2000 | Perrone, Jr. et al. |
| 6,228,119 B1 | 5/2001 | Ondrla et al. |
| 6,589,248 B1 | 7/2003 | Hughes |
| 6,749,638 B1 | 6/2004 | Saladino |
| 6,855,150 B1 | 2/2005 | Linehan |
| 6,926,738 B2 | 8/2005 | Wyss |
| 6,942,475 B2 | 9/2005 | Ensign et al. |
| 7,105,027 B2 | 9/2006 | Lipman et al. |
| 7,150,761 B2 | 12/2006 | Justin et al. |
| 7,175,665 B2 | 2/2007 | German et al. |
| 7,309,363 B2 | 12/2007 | Dietz |
| 7,429,346 B2 | 9/2008 | Ensign et al. |
| 7,618,422 B2 | 11/2009 | Goodwin |
| 7,749,276 B2 | 7/2010 | Fitz |
| 8,425,614 B2 | 4/2013 | Winslow et al. |
| 2003/0069644 A1 | 4/2003 | Kovacevic et al. |
| 2004/0049284 A1 | 3/2004 | German et al. |
| 2004/0236428 A1 | 11/2004 | Burkinshaw et al. |
| 2005/0027365 A1 | 2/2005 | Burstein et al. |
| 2005/0075736 A1 | 4/2005 | Collazo |
| 2005/0165492 A1 | 7/2005 | Fitz |
| 2005/0222685 A1 | 10/2005 | Hayden et al. |
| 2006/0015184 A1 | 1/2006 | Winterbottom et al. |
| 2006/0069444 A1 | 3/2006 | Deffenbaugh |
| 2006/0100714 A1 | 5/2006 | Ensign |
| 2006/0190086 A1 | 8/2006 | Clemow et al. |
| 2007/0118141 A1 | 5/2007 | Marchyn et al. |
| 2008/0114464 A1 | 5/2008 | Barnett et al. |
| 2008/0243260 A1 | 10/2008 | Lee et al. |
| 2008/0300689 A1 | 12/2008 | Mc Kinnon et al. |
| 2012/0101584 A1 | 4/2012 | Amirouche et al. |
| 2013/0166035 A1 | 6/2013 | Landon |
| 2014/0094818 A1 | 4/2014 | Wallace et al. |

OTHER PUBLICATIONS

Journey, "Bi-Cruciate Stabilized Knee System", Copyright 2006, 20 pages.
Stryker, "Triathlon Knee System / Express Instruments Surgical Protocol", copyright 2007.
Stryker, "Triathlon Knee System / Patella Preparation & Trialing Kit Contents—Lower Tray".
Stryker, "Triathlon Knee System / Size 3-6 CR Femoral Tibial Trialing Kit Contents—Lower Tray".
Stryker, "Triathlon with Single-Use Instrumentation / Optimize your TKA Experience", 2011.
Stryker, Triathlon Knee System Surgical Protocol, 2010.
Zimmer® CAS—ICE Cube™ Instruments, © 2009.

MODULAR PATELLA TRIALS

CROSS-REFERENCE TO RELATED APPLICATIONS

The present application is a continuation of U.S. patent application Ser. No. 16/157,344, filed on Oct. 11, 2018, and issued as U.S. Pat. No. 11,013,606, which is a continuation of U.S. patent application Ser. No. 14/208,586, filed on Mar. 13, 2014, and issued as U.S. Pat. No. 10,130,480, which claims the benefit of the filing date of U.S. Provisional Application No. 61/780,641, filed Mar. 13, 2013, the disclosures of which are hereby incorporated herein by reference.

BACKGROUND OF THE INVENTION

A tri-compartmental, or total, knee joint replacement includes the preparation and resurfacing of the femur, tibia and patella bones. Briefly, the surgical procedure involves calculated bone resections of each bone with the goal of replacing damaged articular cartilage, restoring the joint line and returning the patient to a pain-free movement of the knee joint.

In order to ensure proper knee joint kinematics, trial components of the femur, tibia and patella are used interoperatively. During the surgery, each bone is resected and the trial components are placed on each respective bone to allow the surgeon to trial the joint through a full range of motion. During trialing, the surgeon assesses the joint line, range of motion and ligament tension. Trial components represent various thicknesses, widths, or profiles to replicate the final implant prosthesis. The trialing process allows the surgeon to ensure proper knee joint function prior to the implantation of the final prosthesis.

Patella trials are an example of trialing instruments in preparation for permanent implants. Implants are known to be modular in which they may be stacked to accommodate individual physiological differences between patients, such as is disclosed in U.S. Patent Application Publication No. 2006/0015184 A1 to Winterbottom et al., the entirety of which is incorporated herein by reference. Current patella trials are known to use at least a 2-piece design. In accordance with U.S. Pat. No. 6,855,150 to Linehan, the entirety of which is incorporated herein by reference, pegs may extend downwardly from an articular surface member and can be inserted into a drill guide to form a combination patellar trial and drill guide. The patellar trial and drill guide may then be inserted into a resected patella and this assembly may then be placed in a femoral groove and run through a range of motion test. If the patellar trial and drill guide is not the appropriate size or is in the wrong location, a different patellar trial and drill guide may be inserted and retested. This method and the devices used for this method has the option of the patella being drilled for the permanent implant after trialing as the drill guide does not have features that mate with pre-drilled holes in the resected patella. Thus, the trialing in Linehan will not be done with a trial implant having the same shape nor placed in the same location as the final permanent implant.

Furthermore, current patella trial systems are offered as reusable instruments distributed in instrument trays. These trialing systems are expensive to manufacture, clean, sterilize and ship. There is currently an entire patella trial designed to represent each patella implant offering in a knee implant system. The problem thus exists that for every surgery an entire system of patella trials, which may be in kit form, need to be cleaned, sterilized and enter the surgical field in an operating room. This is very expensive, inefficient and increases the risk of infection due to increased instrumentation in the operating room.

There exists a need for a new patella trialing system which maximizes the surgeons interoperative flexibility while minimizing instrument costs, minimizing cleaning/sterilization costs and minimizing the chance of infection.

BRIEF SUMMARY OF THE INVENTION

The present invention is directed to a modular patella trial, trial kit, and corresponding system that may include patella trials having the same size, shape, and configuration as the permanent patella prosthetic device intended to be mimicked.

This trial system may include an articular element or button and may include a sizing element. The articular element may have a length, width, and thickness. The articular element may be symmetric about a central axis, symmetric about a plane, or asymmetric. The articular element commonly may have a cylindrical or egg-shaped cross-section in which an extension is added to the cylindrical section. The articular element may have a posterior surface and an anterior surface separated by the thickness of the articular element. In some instances, the anterior surface may be flat. In addition, the posterior surface may have an articular surface profile corresponding to an articular surface profile of a patella prosthesis. At least one protrusion or peg may extend outwardly from the anterior surface.

In accordance with one aspect of the invention, the trial system may have a single sizing element. The sizing element may have a length, a width, and a thickness. The sizing element may have a posterior surface and an anterior surface separated by the thickness of the sizing element. The sizing element may have at least one aperture that may extend through the posterior and anterior surfaces of the sizing element. Although the sizing element may have more or fewer, a sizing element typically will have three apertures. Each aperture may be adapted to receive a corresponding peg or protrusion of the articular element. In some instances, the aperture and the protrusion may be cylindrical. When the protrusion is inserted into the aperture, the modular patella trial system may then have a thickness substantially equal to the total of the thicknesses of the articular element and the sizing element.

The articular and sizing elements of this trial system may be either reusable or disposable. Thus, these elements may be metallic wherein they may be made of materials such as but not limited to stainless steel, titanium, or cobalt chromium alloy; plastic wherein they may be made of materials such as but not limited to polyethylene, phenolic, epoxy, acrylic, delrin; or ceramic.

The trial system may have a second sizing element in addition to the first sizing element. The second sizing element may have a length, a width, and a thickness. The second sizing element may have a posterior surface and an anterior surface separated by the thickness of the second sizing element. The second sizing element may have at least one aperture that may extend through the posterior and anterior surfaces of the sizing element. Each aperture may be adapted to receive a corresponding protrusion of the articular element. Like the first sizing element, the aperture and the protrusion may be cylindrical. A modular patella trial system having a second sizing element will have a thickness substantially equal to the total of the thicknesses of the articular element, the first sizing element, and the second sizing element.

In some instances, the trial system may have all of the features in the first aspect as well as additional features. The anterior surface of the articular element may further have at least one locking feature that extends outwardly from the anterior surface. In this instance, the sizing elements may each have a corresponding locking aperture such that each locking aperture may be adapted to receive a locking feature. The locking features and apertures will often be cylindrical in shape. In some arrangements, the trial system may have two or more locking features and two or more corresponding locking apertures such that each locking aperture is adapted to receive one of the locking features.

In accordance with another aspect of the invention, a modular patella trial is provided. The modular patella trial may include an articular element and may include at least one sizing element. The articular element may have a length, a width, and a thickness. The articular element may have a posterior surface and an anterior surface. The posterior and anterior surfaces may be separated by the thickness of the articular element. The anterior surface may have at least one protrusion. The one or more protrusions may extend outwardly from the anterior surface of the articular element.

Any of the sizing elements in accordance with this aspect may have a length, width, and thickness. Any such sizing elements may have a posterior surface and an anterior surface. The posterior and anterior surfaces may be separated by the thickness of the one or more sizing elements. Such sizing elements may have at least one aperture extending through posterior and anterior surfaces of the sizing elements. The one or apertures of the sizing element may be capable of receiving a corresponding protrusion of the articular element. In some such arrangements, the modular patella trial may have a thickness substantially equal to the total of the thicknesses of the articular element and one or more sizing elements used in conjunction with the articular element.

In accordance with another aspect of the invention, a modular patella trial system may be provided. The modular patella trial system may include an articulating surface element and at least one mating element. The articulating surface element may have a length, a width, and a thickness. The articulating surface element may have a posterior surface and an anterior surface. The posterior and anterior surfaces may be separated by the thickness of the articulating surface element. The articulating surface element may have an outer surface. The articulating surface element may have at least one tongue extending outwardly from the outer surface.

Any of the mating elements in accordance with this aspect may have a length, a width, and a thickness. The one or more mating elements may have a posterior surface and an anterior surface. The posterior and anterior surfaces may be separated by the thickness of the corresponding mating element. The one or more mating elements may have an exterior surface. The one or more mating elements may have at least one groove extending inwardly from the exterior surface. The one or more grooves of any of the mating elements may be adapted to receive a corresponding tongue of the articulating surface element. In some such arrangements, the modular patella trial system may have a thickness substantially equal to the total of the thicknesses of the articulating surface element and the one or more mating elements used in conjunction with the articulating surface element.

In accordance with another aspect of the invention, a modular patella trial system is provided. The modular patella trial system may include an articular button and a bone protector plate. The articular button may have a length, a width, and a thickness. The articular button may include a posterior surface and an anterior surface. The posterior and anterior surfaces may be separated by the thickness of the articular button. The anterior surface may have at least one protrusion. The one or more protrusions may extend outwardly from the anterior surface.

The bone protector plate in accordance with this aspect may be capable of placement onto a resected surface of a patella. The bone protector may have a length, a width, and a thickness. The bone protector plate may include a posterior surface and an anterior surface. The posterior and anterior surfaces may be separated by the thickness of the bone protector plate. At least one fixation cavity may extend into the posterior surface of the bone protector plate. At least one peg may extend from the anterior surface of the bone protector plate. The one or more fixation cavities may be capable of receiving a corresponding protrusion of the articular button. The one or more pegs may be capable of insertion into at least one cavity on the resected surface of the patella.

In accordance with another aspect of the invention, a method for reconstructing a patella of a patient is provided. In such an aspect, a portion of the structure of a patella to be removed may be determined. The predetermined portion of the patella, which may be a posterior portion, may be removed to form a resected surface. A thickness of the resected patella may be determined. A peg preparation instrument may be placed against the resected surface of the patella. The peg preparation instrument may have an anterior surface and a posterior surface. The anterior and posterior surfaces may be separated by a thickness. The peg preparation instrument may have at least one opening through the thickness. The opening may be capable of receiving a boring instrument through the entire thickness. At least one hole may be bored into the resected surface of the patient's patella. A surface profile of the patella may be determined. The peg preparation instrument may be removed from contact with the resected surface of the patella. A preselected bone protector plate may be placed on the resected surface of the patella. The bone protector plate may have at least one protrusion. The one or more protrusions may extend from the bone protector plate. The bone protector plate may have at least one fixation cavity. The protrusion may be removably inserted into the one or more holes of the resected surface of the patella. The bone protector plate may have a profile substantially corresponding to the profile of the resected patella. A preselected articular button may be placed on the bone protector plate. The articular button may have a posterior surface and an anterior surface. The posterior surface may have a profile. The anterior surface may have at least one peg. The posterior and anterior surfaces may be separated by the thickness of the articular button. The one or more pegs of the articular button may be removably inserted into the cavity of the bone protector plate to form a trial assembly of the articular button, the bone protector plate, and the patella. The bone protector plate may be removed from contact with the resected surface of the patella. A proper permanent implant may be determined for insertion into the one or more holes of the resected surface of the patella. The permanent implant may be inserted into the one or more holes on the resected surface of the patella.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body. The term "step of" does not mean "step for."

Figure 1:
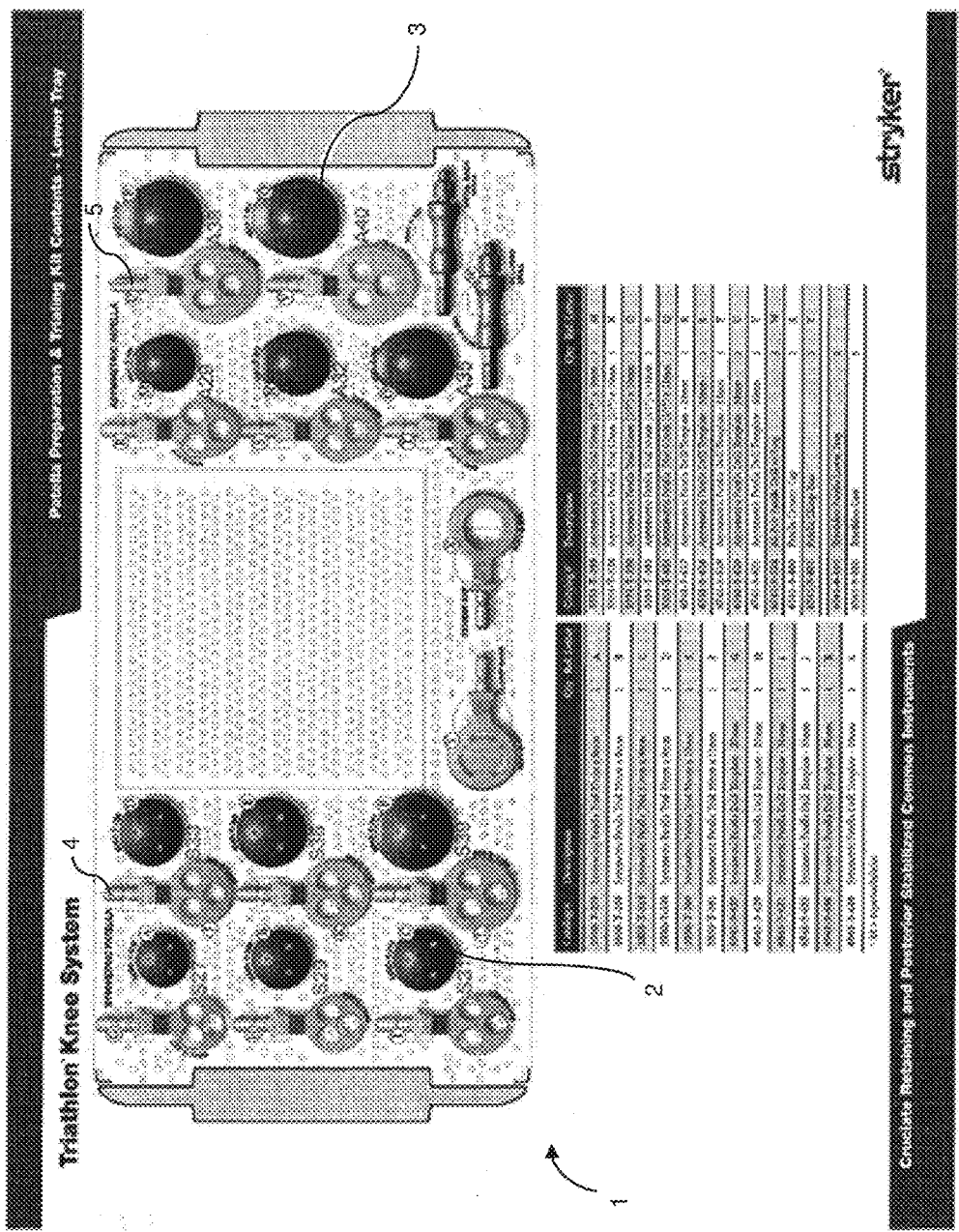
FIG. 1 is a view of a Stryker® Corp. Triathlon® Patella Preparation and Triathlon® Kit Components for the Triathlon® Knee System, as known in the prior art.

Referring now to the drawings, FIG. 1 illustrates the lower tray of the prior art Triathlon® Patella Preparation and Triathlon® Kit Components for the Triathlon® Knee System. These instruments form part of a standard Triathlon® Knee System and the tray contents are identified in the table of FIG. 1. Currently a patella trial kit 1 includes individual trial implants of various lengths, widths and thicknesses. Such a kit includes various sizes of a symmetric patella trial 2, an asymmetric patella trial 3, and a patella drill template 4, as well as other instruments such as a clamp base 5 and a cement cap 6. This current approach to patella trial distribution requires significant space in instrument trays which takes up room in an operating room as well as central supply in the hospital and necessitates additional shipping costs for instruments that will not be used where they are delivered. Further, the current patella trials are reusable and require a cleaning and sterilization cycle between each use. The surgical decision between using a symmetric or an asymmetric design may be based on surgical preference, patient anatomy, design of the trochlear groove of a corresponding femoral implant, or other known influences.

Figure 2:
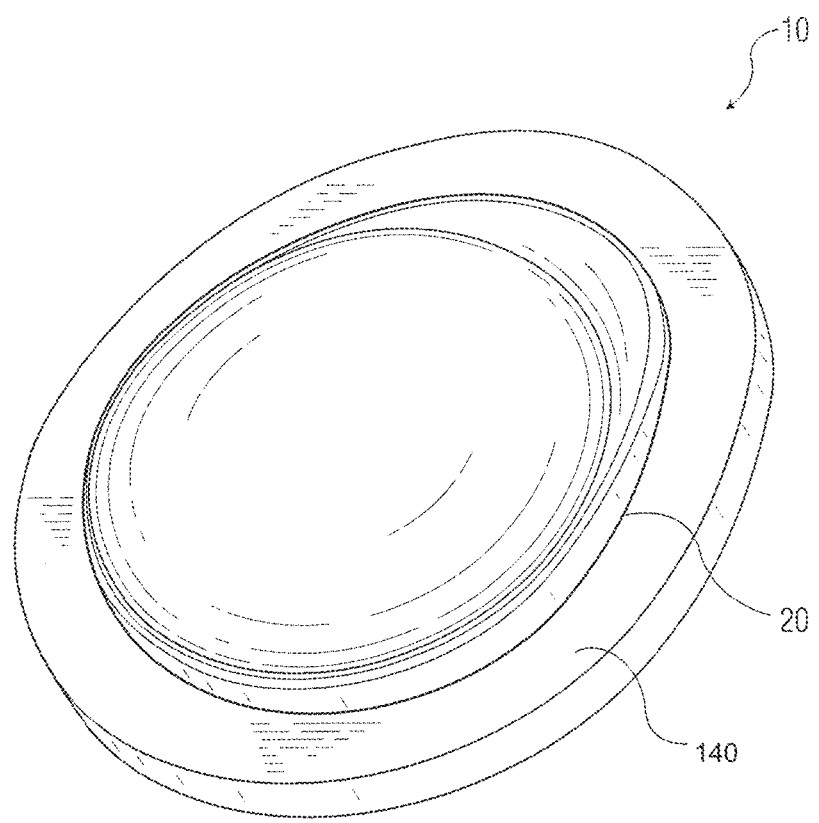
FIG. 2 is a perspective view of a modular patella trial in accordance with an embodiment of the present invention.
Figure 3:
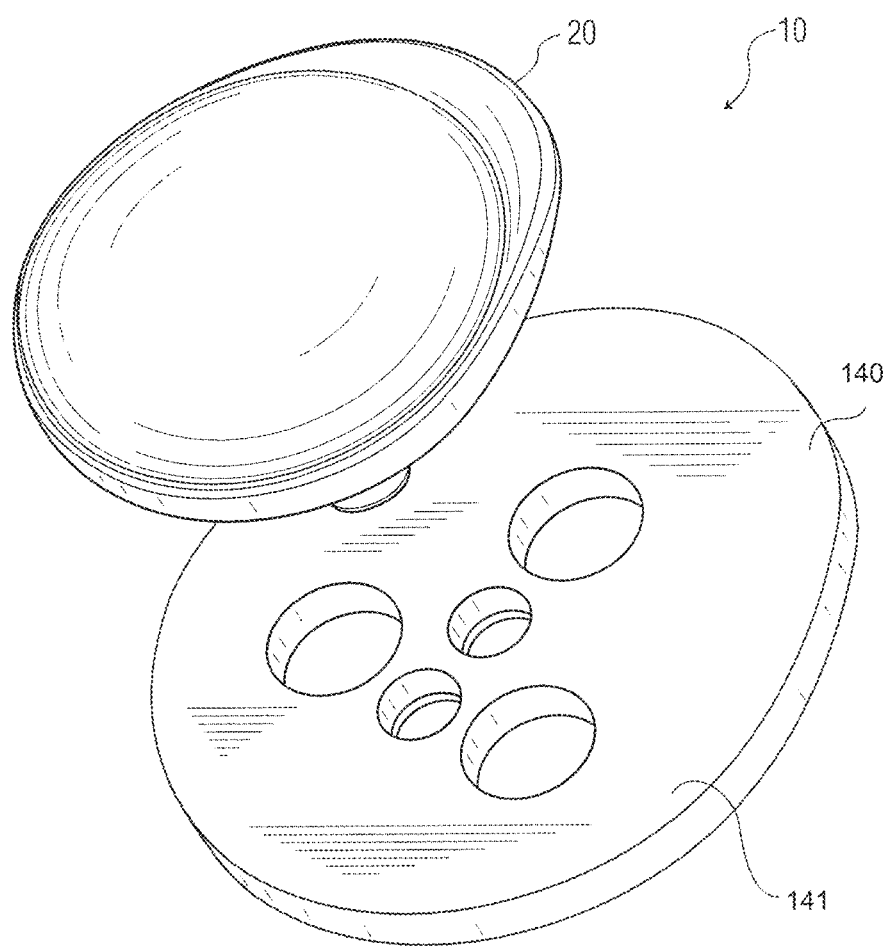
FIG. 3 is an exploded perspective view of the modular trial shown in FIG. 2.
Figure 4:
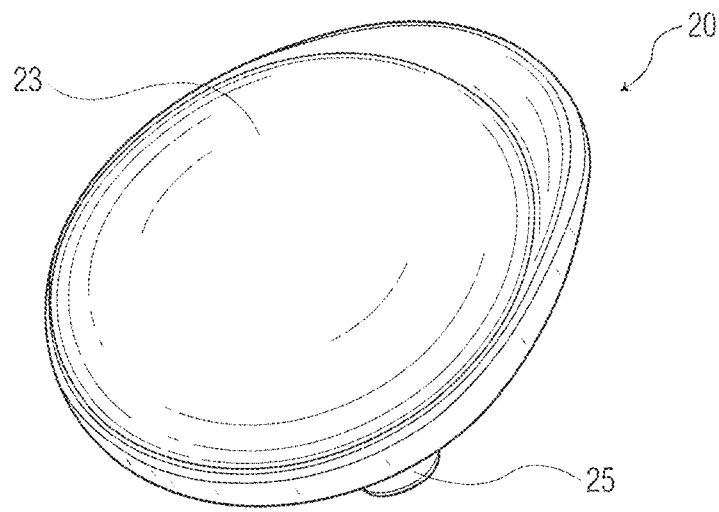
FIG. 4 is a perspective view of an articular element shown in FIG. 2.
Figure 5:
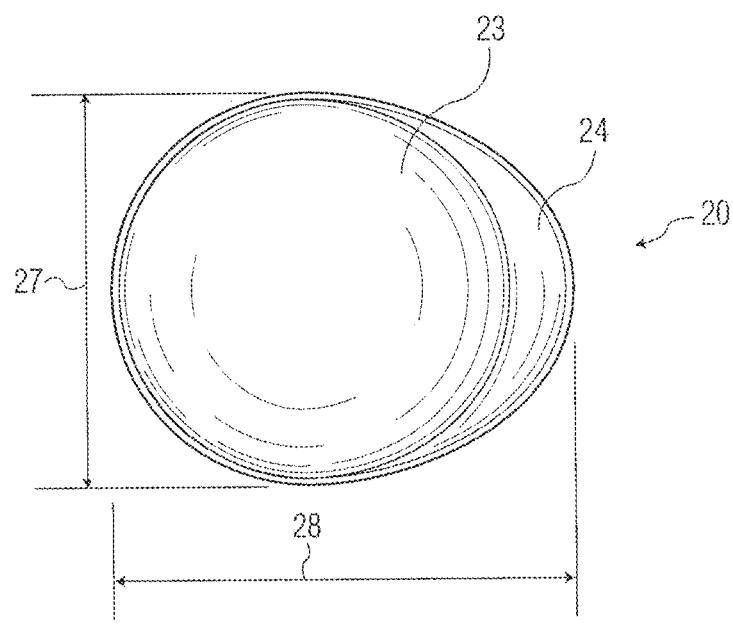
FIG. 5 is a plan view of a posterior surface of the articular element shown in FIG. 2.
Figure 6:
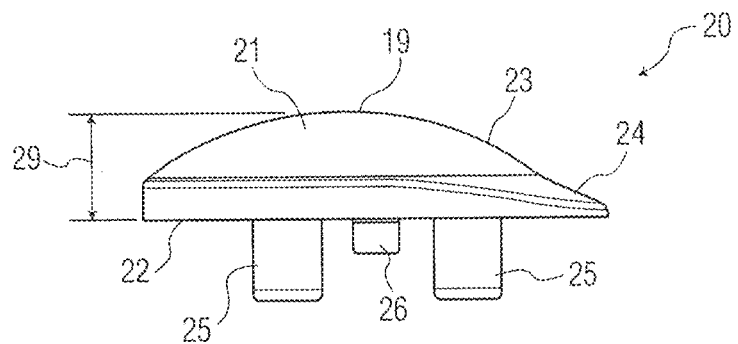
FIG. 6 is a side view of the articular element shown in FIG. 2.
Figure 7:
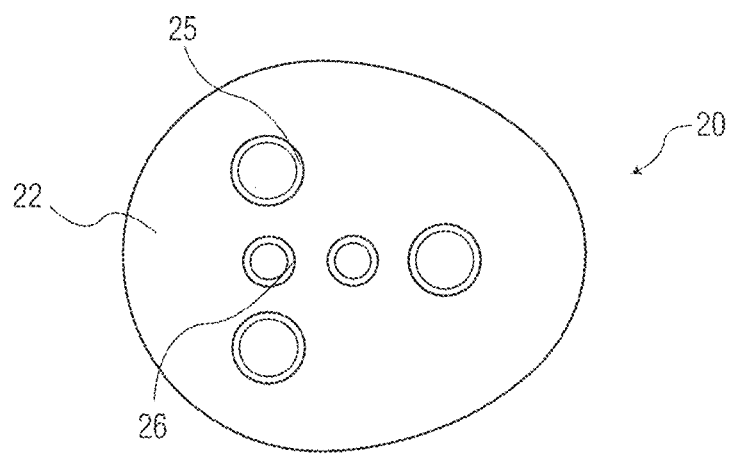
FIG. 7 is a plan view of an anterior surface of the articular element shown in FIG. 2.
Figure 8:
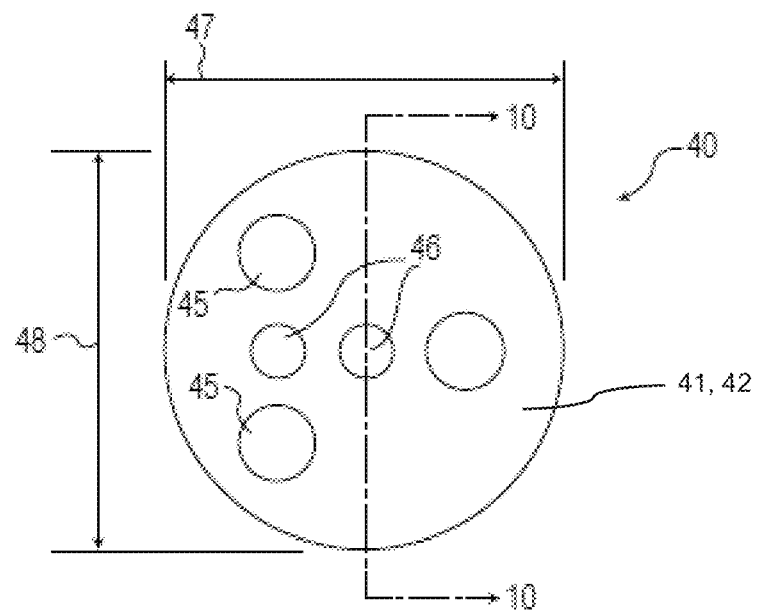
FIG. 8 is a plan view of a posterior surface of a symmetric sizing element in accordance with an embodiment.

FIGS. 2-3 illustrate one embodiment of the modular patella trial assembly of the present invention generally denoted as 10. The assembly 10 is comprised of an articular element or articular button 20 and a sizing element 140, as shown in FIGS. 2-3, a sizing element 40 as shown in FIGS. 8-9, or other sizing elements in accordance with an embodiment. It is envisioned that a modular patella trial kit would include a single articular element 20 and differently sized sizing elements 40, 140 which can be assembled interoperatively to enhance a surgeon's options during a knee operation. A single articular element 20 can be provided because the articular surface used in patella implant systems, for various sizes, is substantially equivalent. Further, there may be separate symmetric and asymmetric patella trial kits which may each include a respective articular element 20 and various sizing elements 40, 140. A symmetric articular element includes a circular articular contour 16. These modular patella trial kits may be designed for either repeated- or single-use. A single-use modular trial kit would have the advantages of minimizing infection, cleaning and sterilization requirements, and the costly distribution cycle seen in standard instrument trays.

FIGS. 4-7 further illustrate one arrangement of a preferred embodiment of the articular element 20. It has a width 27, length 28 and thickness 29. The articular element 20 includes a posterior surface 21 in which the outer extremity is a posterior end 19 and an articular profile 23, a generally planar anterior surface 22, and an asymmetric extension 24. The posterior surface 21 and the anterior surface 22 are separated to produce the thickness 29. The articular surface profile 23 is a three-dimensional design covering the posterior surface of the trial and replicates the articular surface profile of a patella implant prosthesis. The asymmetric extension 24 in such an arrangement is integrated with and extends laterally from the articular contour 16 in the direction of the length 28. However an alternate arrangement of a patella trial that is symmetric about an axis through the width of the articular element would exclude this extension feature. Protrusions or peg features 25, which may be in the form of projections as shown, extend in a substantially perpendicular direction from the planar anterior surface 22 of the articular element 20. Situated among the protrusions 25 are locking features 26, which may be in the form of projections as shown, that also extend perpendicularly from the anterior surface 22 and may be used to orient the articular element 20 in a predetermined rotation relative to the sizing element 40 and may be used to lock, such as through an interference fit, the articular element 20 with a sizing element, such as those described herein. While the arrangement shown contains three protrusions or pegs 25 and two locking features 26, alternate arrangements may include various numbers of both protrusions 25 and the locking features 26. Further, the protrusions 25 and the locking features 26 are oversized circular posts in this configuration, but may be in other shapes in alternative embodiments not shown. Also, while the protrusions 25 are arranged in a triangular fashion and the locking features 26 are arranged among and between the protrusions 25, alternative arrangements of either of these elements are within the scope of this invention.

FIGS. 8 and 9 illustrate one arrangement of a preferred embodiment of a sizing element 40 having a width 47, length 48, and thickness 49 as well as posterior and anterior surfaces 41, 42. The sizing element 40 is a female member of the trial kit adapted to receive the pegs or protrusions 25 of articular element 20 that serve as the male member of the modular patella trial 10. In the symmetric configuration of the sizing element 40 shown, the width 47 and length 48 are substantially similar. The sizing element 40 includes three apertures 45 and two locking apertures 46 capable of receiving the protrusions 25 and the locking features 26, respectively, of the articular element 20. In the arrangement shown, the apertures 45 are circular and have substantially the same cross-section as the locking features 26 of the articular element 20. Furthermore, the locking apertures 46 extend completely through the thickness 49 of the sizing element 40 and each of the apertures 45 and locking apertures 46 are oriented in a substantially normal direction to the posterior and anterior surfaces of the sizing element 40. Alternative configurations of sizing element 40 may include various quantities and various shapes and dimensions of apertures 45 and locking apertures 46 which are capable of receiving the protrusions 25 and locking features 26 of the articular element 20, respectively.

As can be seen in the cross-sections of a sizing element 40 shown in FIGS. 9A-9E, multiple arrangements of sizing element 40 may be present in a kit of a modular patella trial 10 in accordance with the present invention. As shown, the length 48 and the thickness 49 may vary among the various sizing elements 40 included in the kit. By having a variety of sizes of sizing elements 40 at their disposal, surgeons have the interoperative flexibility to optimize the fit of the modular patella trial 10 that will lead to the eventual implantation of the appropriate permanent patella implant prosthesis.

Figure 10:
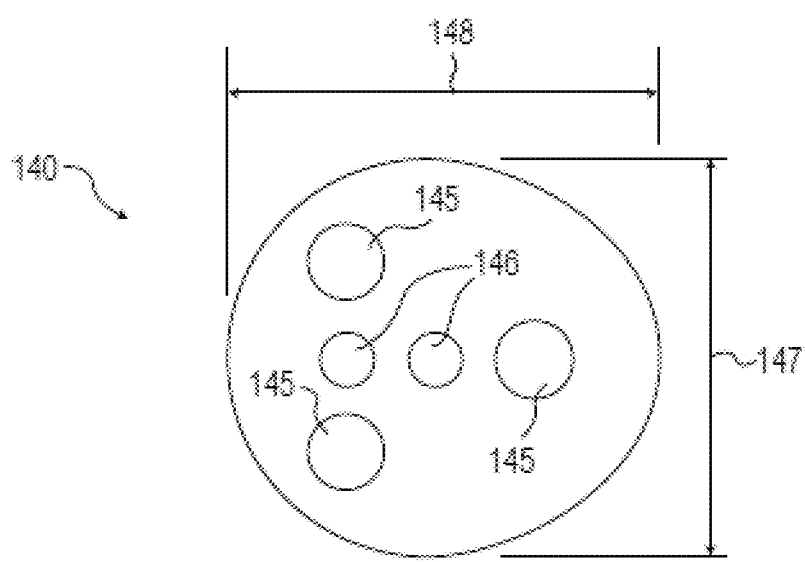
FIG. 10 is a plan view of a posterior surface of the sizing element shown in FIG. 2.
Figure 9A:
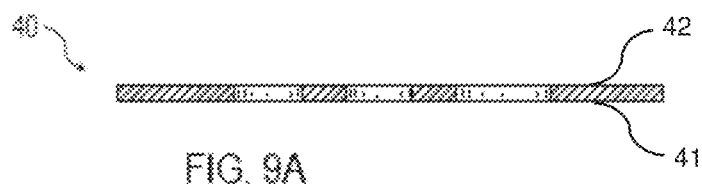
FIGS. 9A-9E are side cross-sectional views of various sizes of a sizing element in accordance with various arrangements.
Figure 9B:
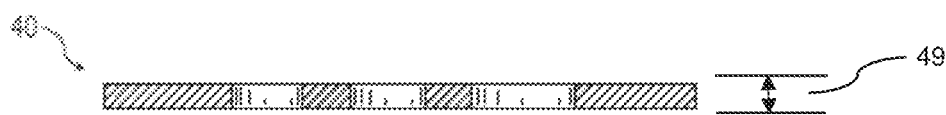
Figure 9C:
Figure 9D:
Figure 9E:

FIG. 10 provides an alternative arrangement of a sizing element. In this asymmetric configuration, which may be used with either symmetric or asymmetric articular elements, a sizing element 140 has a width 147, length 148, and thickness 149 in addition to posterior and anterior surfaces 141, 142 in which the width 147 is less than the length 148 and the posterior and anterior surfaces 141, 142 are separated by the thickness 149. In some arrangements, the length 148 may be oriented in a medial-lateral direction to provide coverage on the resected patella. This configuration of sizing element 140 may include three circular apertures 145 extending through the thickness 149 and two circular locking apertures 146, all arranged in the same manner as their counterpart apertures 45 and locking apertures 46 in the sizing element 40 shown in FIG. 7. The sizing element 140 similarly may be capable of receiving the protrusions 25 and the locking features 26 of the articular element 20. Again, alternative configurations may include various quantities, shapes, and arrangements of apertures 145 and locking apertures 146.

Figure 11:
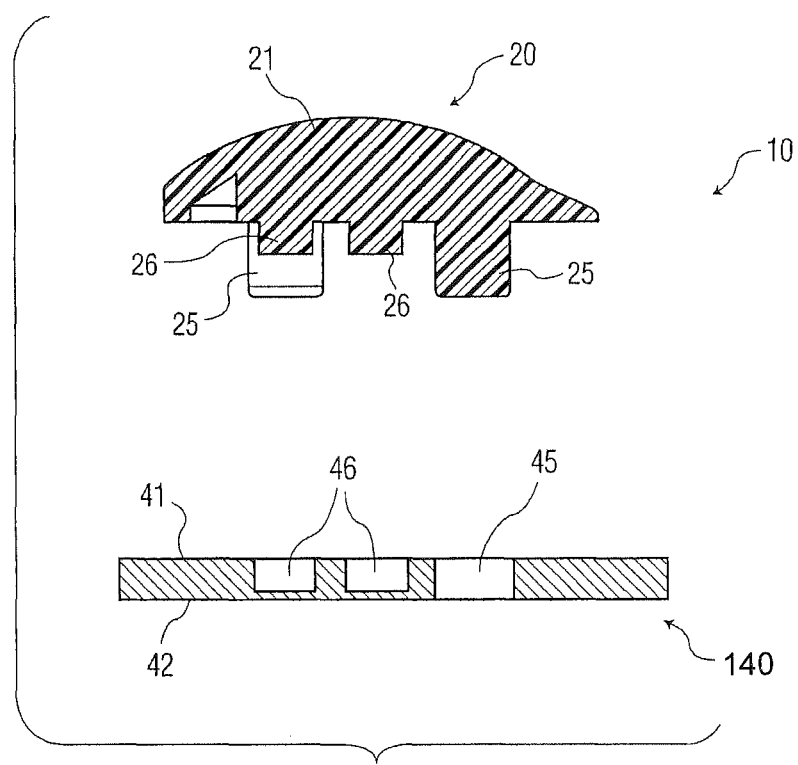
FIG. 11 is an exploded side cross-sectional view of the elements of the modular patella trial shown in FIG. 2.
Figure 12:
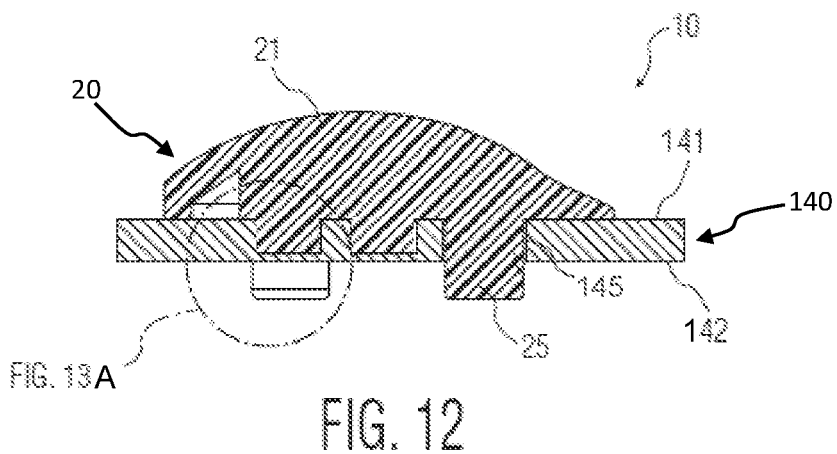
FIG. 12 is a side cross-sectional view of the modular patella trial shown in FIG. 2.

FIG. 11 is an exploded cross-sectional side view of the modular patella trial 10 showing the relative orientations and arrangements of the protrusions 25, locking features 26, apertures 45 and locking apertures 46 prior to insertion of the articular element 20 into the sizing element 140. FIG. 12 illustrates the assembled modular patella trial 10. As shown in the figure, the protrusions 25 locate within the apertures 145 and the locking features 26 engage the locking apertures 146. The modular patella trial 10 is designed with clearance between protrusions 25 and apertures 45.

Figure 13A:
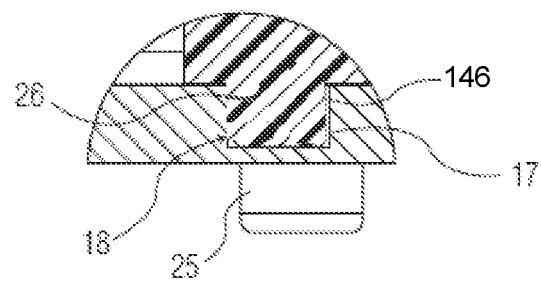
FIG. 13A is a detailed view of a portion of the modular patella trial shown in FIG. 2, as highlighted in FIG. 12.

As best shown in FIGS. 12 and 13A, protrusions 25 have a length such that they extend through the sizing element and are capable of being inserted into a cavity on the posterior surface of a prepared patella bone 150 during the surgical trialing process. Also shown in FIG. 13, the locking features 26 have an outer surface 17 that engages an inner surface of locking apertures 146. In the arrangement of the preferred embodiment of FIGS. 12 and 13A, the outer surface 17 of the locking features 26 is cylindrical and has a slightly larger diameter than the inner surface 18 of the locking apertures 146, creating an interference fit to provide the force required to hold the modular patella trial together during the surgical trialing process. Although the locking features 26 and locking apertures 46 are shown as being cylindrical in FIG. 12, alternative arrangements may have additional shapes of these features, and these elements may engage one another using other methods rather than an interference fit engagement. Further, the locking features 26 and locking apertures 46 may be arranged to provide a rotational alignment of the articular profile 23 and asymmetric extension 24 in an asymmetric trial embodiment. For example, in the configuration shown in FIG. 12, one locking feature 26 and one corresponding locking aperture 46 are located off-center and one locking feature and one corresponding locking aperture are located on-center such that the articular element 20 can only be inserted in one orientation into the sizing element 140.

Figure 13B:
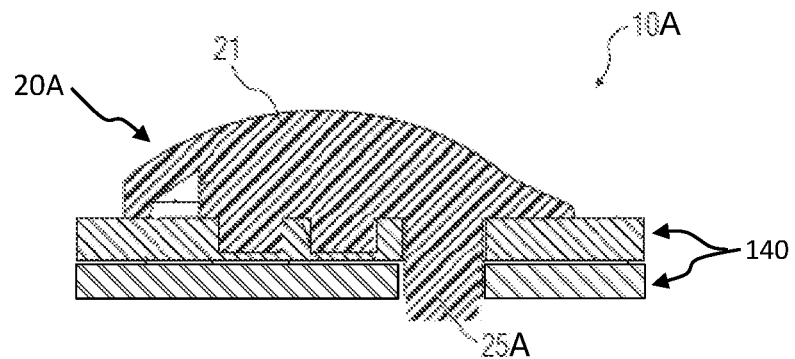
FIG. 13B is a side cross-sectional view of the modular patella trial shown in FIG. 2 along with an additional sizing element in accordance with an embodiment.

In alternative arrangements of a modular patella trial kit, there may be separate articular elements specific for the length and width and separate sizing elements specific for the thickness. Further, as shown in FIG. 13B, modular patella trial 10A may include an articular element 20A that may interface with a second or additional sizing elements 140 of the same or different thicknesses to form a modular patella trial. In this arrangement, protrusions 25A of the articular element 20A may have a length such that they extend through the apertures of each sizing element 140 of the patella trial and are still capable of being inserted into a cavity on the posterior surface of a prepared patella bone during a surgical trialing process.

Figure 14:
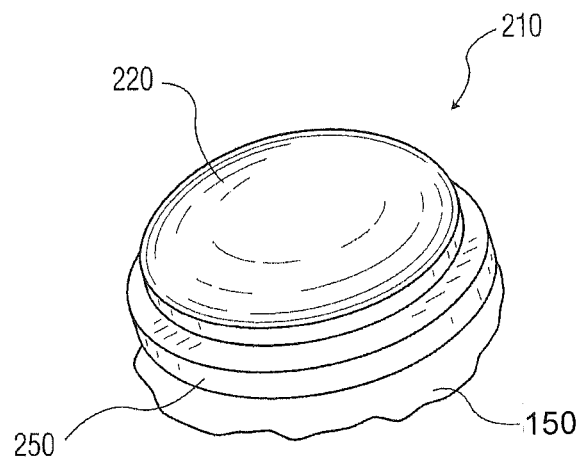
FIG. 14 is a perspective view of a modular patella trial assembly in accordance with an embodiment of the present invention.

Referring now to FIG. 14, in an alternative embodiment of the present invention, a modular trial assembly 210 may be inserted into a patient's prepared patella to serve as a temporary prosthetic device. This assembly 210 may include an articular button 220 and a bone protector plate 250 in which the plate 250 is adapted for insertion into a patient's patella 150. As shown in FIGS. 16-19, the articular button 220 has a width 227, length 228 and thickness 229. The articular button 220 includes a posterior surface 221 in which the outer extremity is a posterior end 219 and an articular profile 223 as well as an anterior surface 222 separated by the thickness 229. The articular surface profile 223 is a three-dimensional design covering the posterior surface of the trial and replicates the articular surface profile of a patella implant prosthesis. Although not shown, an articular button may include an asymmetric extension, similar to the asymmetric extension 24 described with respect to the modular patella trial assembly 10, that is integrated with and extends from the articular profile 223 in the direction of the length 228. In the arrangement shown in FIGS. 16-19, the articular button 220 is symmetric about an axis through the width 227. Protrusions or peg features 225, which may be in the form of projections as shown, extend in a substantially perpendicular direction from the anterior surface 222. While the arrangement shown contains three protrusions 225, alternative arrangements may include various quantities of protrusions 225. Further, protrusions 225 have a circular cross-section in this configuration, but other cross-sections, such as a triangular or rectangular cross-section, may be used in alternative arrangements. Also, while protrusions 225 are arranged in a triangular fashion, alternative arrangements are contemplated by this invention.

FIGS. 16 and 20-22 illustrate one arrangement of a preferred embodiment of a bone protector plate 250 having a width 257, length 258, and thickness 259 as well as posterior and anterior surfaces 251, 252. The width 257 and length 258 correspond to a profile of the bone protector plate 250. In the symmetric configuration shown, the width 257 and length 258 are substantially similar. As the female interface for the articular button 220, the bone protector plate 250 shown includes three fixation cavities 254 capable of receiving the protrusions 225 of the articular button 220. In the arrangement shown, the fixation cavities 254 are cylindrical, extend from the posterior surface 251 through a large portion of the thickness 259 of the bone protector plate 250 but not the entire thickness 259, and are oriented in a substantially normal direction to the posterior surface 251. The protector plate 250 shown further includes pegs 253 that extend from and in a direction substantially normal its anterior surface 252.

Figure 23:
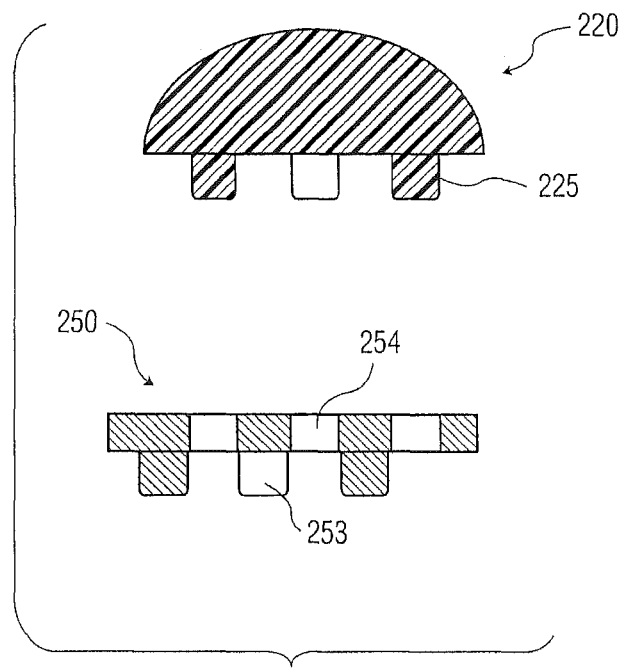
FIG. 23 is an exploded side cross-sectional view of the modular patella trial assembly of FIG. 14.

FIG. 23 provides an alternative arrangement of a bone protector plate. In this asymmetric configuration, the bone protector plate 350 may include all of the features of the bone protector plate 250 shown in FIGS. 16 and 20-22 but may additionally include an asymmetric extension 356. Such an extension 356 stretches along a width 357 of the bone protector plate 250, extends to a length 358, has a thickness 359, and has an articular profile 355 to conform to the trochlear groove of certain patients during a knee operation.

FIG. 23 is an exploded cross-sectional side view of the modular patella trial assembly 210 showing the relative orientations and arrangements of the protrusions 225 of the articular button 220 and the fixation cavities 254 of the bone protector plate 250 in the symmetric configuration prior to insertion of the articular button 220 into the bone protector plate 250. The modular patella trial assembly 210 is designed with clearance between the protrusions 225 and the fixation cavities 254. Alternative configurations of the bone protector plate 250 may include various quantities and shapes of fixation cavities which are capable of receiving the protrusions of the articular button. The articular button 220 may be inserted into the bone protector plate 350 having an asymmetric configuration in the same manner as the button 220 inserts into the bone protector plate 250 having a symmetric configuration.

Figure 24:
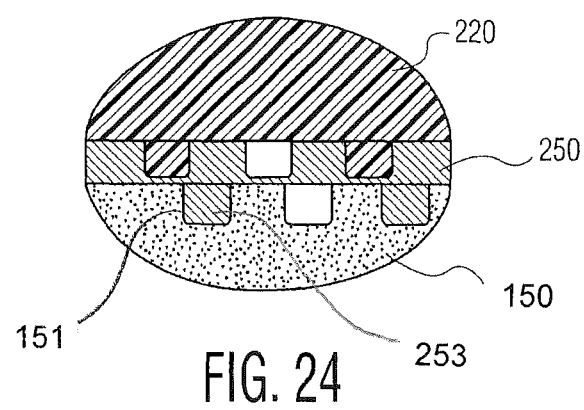
FIG. 24 is a side cross-sectional view of the modular patella trial assembly shown in FIG. 14 inserted into a prepared patella bone.

FIG. 24 illustrates the modular patella trial assembly 210 inserted into a prepared patella bone 150. As shown in the figure, the protrusions 225 of the articular button 220 locate within the fixation cavities 254 of the bone protector plate 250. As further illustrated in FIG. 24, the pegs 253 may be inserted into cavities 151 of the prepared patella 150 prepared for engagement with the anterior surface 252 and the pegs 253 of the bone protector plate 250.

Figure 15:
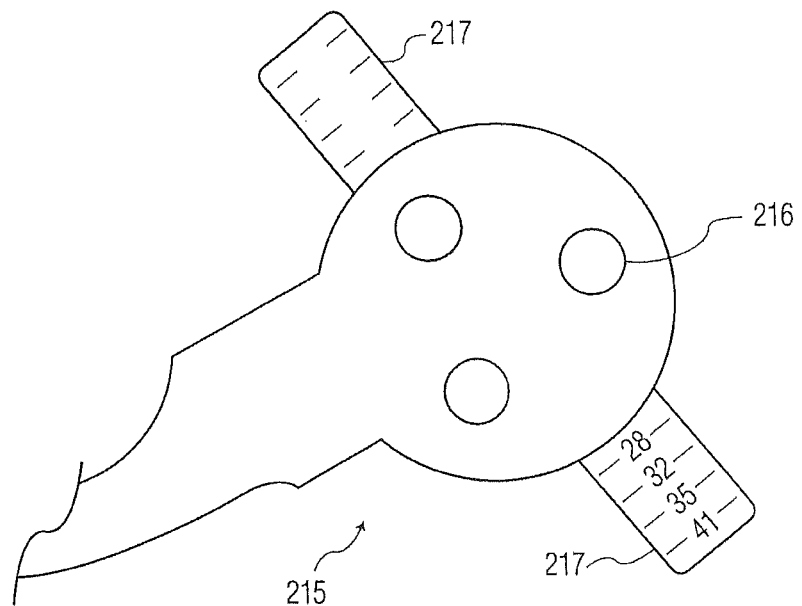
FIG. 15 is a perspective view of a peg preparation instrument for use in the preparation of the modular patella trial assembly of FIG. 14.
Figure 16:
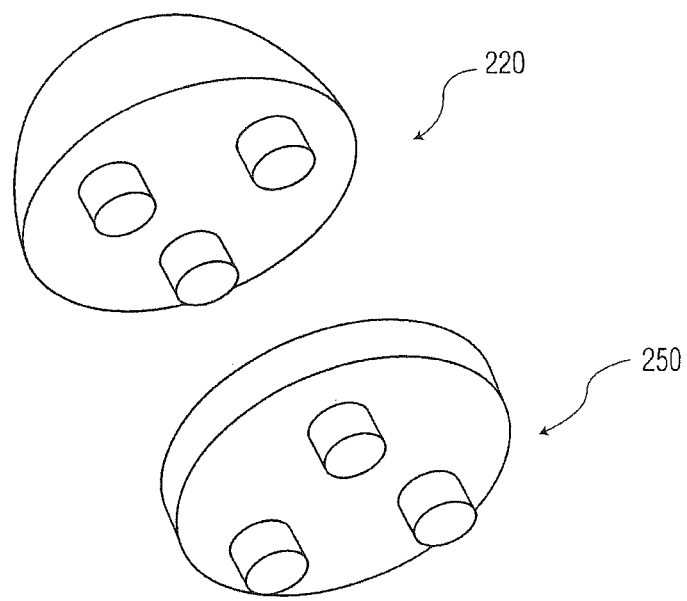
FIG. 16 is an exploded perspective view of an articular button and a bone protector plate of the modular patella trial assembly shown in FIG. 14.
Figure 17:
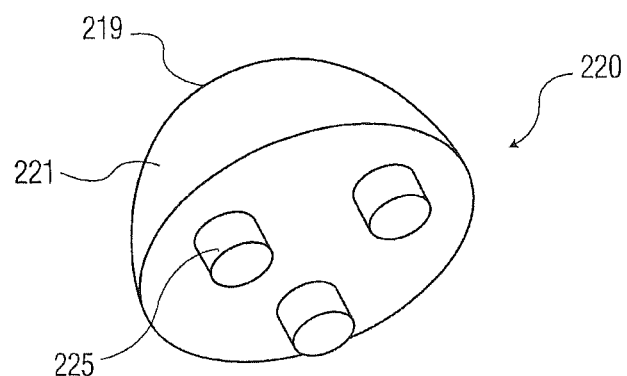
FIG. 17 is a perspective view of the articular button shown in FIG. 14.
Figure 18:
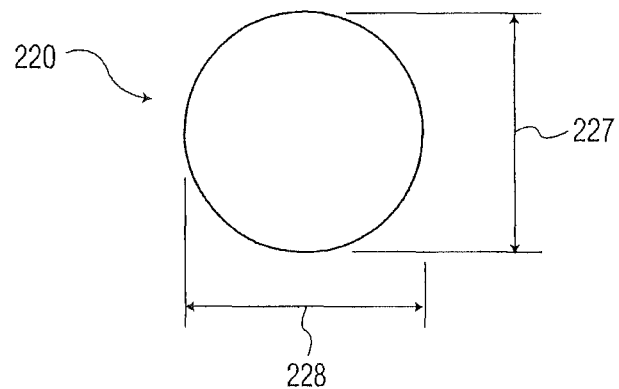
FIG. 18 is a plan view of a posterior surface of the articular button shown in FIG. 14.
Figure 19:
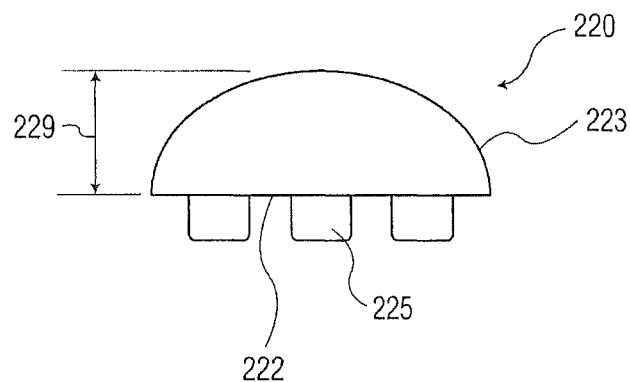
FIG. 19 is a side view of the articular button shown in FIG. 14.
Figure 20:
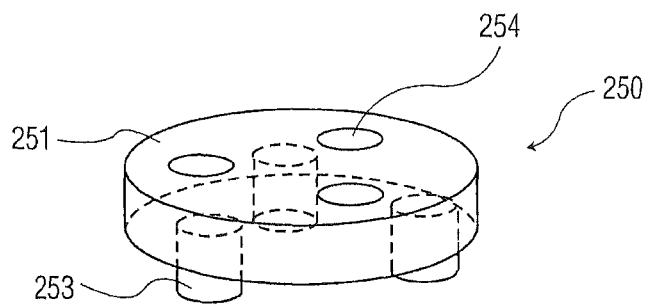
FIG. 20 is a perspective view of the bone protector plate shown in FIG. 14.
Figure 21:
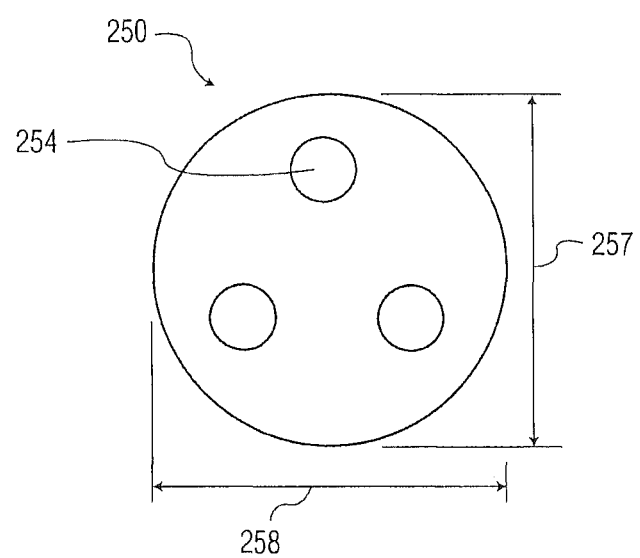
FIG. 21 is a plan view of a posterior surface of the bone protector plate shown in FIG. 14.
Figure 22:
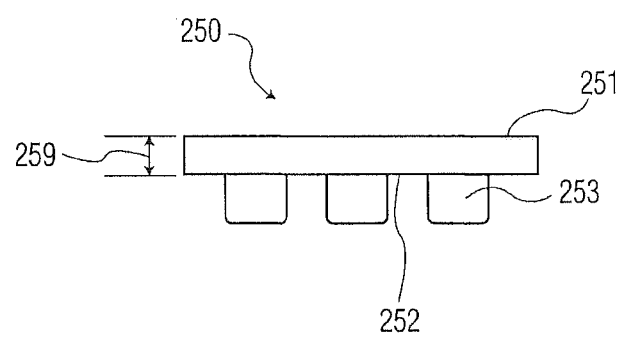
FIG. 22 is a side view of the bone protector plate shown in FIG. 14.

Preparation of a patient's patella for insertion of a modular patella trial begins by pulling the patient's patella away from the patient's trochlear groove of the femur or femoral implant and, in general, facing the anterior surface of the patella toward a medical practitioner. The practitioner may then remove any osteophytes and synovial insertions around the patient's patella. A medical practitioner may then measure the thickness of the patella using a caliper or another capable measuring device and determine an appropriate depth to which the patella should be cut. A practitioner may then resect the patella using any capable instrument, such as a 0.050" non-offset sawblade. The posterior surface of the resected patella will in most cases be flat. The practitioner will then remeasure the thickness of the patient's patella and based on the measurement will place an appropriate patellar drill guide, such as a patella drill template 4 shown in FIG. 1 or peg preparation instrument 215 as shown in FIG. 15, and align such instruments against the resected patella, generally centered upon the patella or as otherwise known in the art. A practitioner may use a clamping device known in the prior art, such as a universal clamp 218 shown in FIG. 25, to maintain the peg preparation instrument 215 or other suitable device against the patella.

In the arrangement shown in FIG. 15, the peg preparation instrument 215 has a flat anterior surface against which the resected patella 150 rests. The instrument 215 may also include fixation holes 216 capable of guiding a boring instrument such as a drill. In the peg preparation instrument 215 shown, there are three fixation holes 216, but any number of fixation holes may be included depending on the number of protrusions or pegs to be inserted into the resected patella 150. The peg preparation instrument 215 further includes opposing marked ears 217 extending substantially in the plane through the posterior surface of the resected patella 150. As shown, the marked ears 217 have equally spaced lines engraved on the posterior surface 251 of the peg preparation instrument 215 that face the medical practitioner after placement of the instrument upon the patient's resected patella 150. Corresponding markings on each ear 217 are labeled 28, 32, 35, and 41 in which the distance between any two corresponding markings is the number labeled next to the engraving, in millimeters. The practitioner then aligns a boring device, such as a conventional medical drill, in a direction substantially perpendicular to the fixation holes 216 of the peg preparation instrument 215 and the resected patella 150. In a preferred arrangement as in the example of FIG. 24, three cavities are then drilled into the resected patella to a depth preferably in a range between 1 mm and 10 mm. However, any number of cavities may be formed using any suitable boring device.

If the medical practitioner decides to use bone cement for the permanent implant, the practitioner must prepare the resected bone surfaces for the bone cement application. The practitioner then removes any residual cartilage and debris which can be washed away. The practitioner may then insert the protrusions of a patella trial, such as the articular element 20 of the modular patella trial 10 or the peg 53 of the bone protector plate 250 as part of a modular patella trial system 200, on the resected patella. In a preferred embodiment using the modular patella trial system 200, the profile of the bone protector plate 250 has a shape that substantially conforms to the shape of the resected patella such that, upon insertion of the bone protector plate 250 into the resected patella 150, the bone protector plate 250 covers substantially all of the resected patella 150. The practitioner next selects an appropriately sized articular component, such as the articular element 20 or the articular button 220, based on the thickness determined to be needed for the patella 150.

A practitioner may take factors such as bone disease, wear marks, and joint laxity to determine an appropriate thickness of a patella trial such as the modular patella trial 10 or the modular patella trial assembly 210. Further, according to known anthropometric data, the average male patella has a 29 mm thickness whereas the average female patella has a 26 mm thickness as measured between the posterior and anterior surfaces. Based on the averages, a medical practitioner may determine the necessary thickness of a modular patella trial or trial assembly by taking the difference between the thickness of the resected patella and the anthropometric data.

In the preferred embodiment using the modular patella trial system 200, upon selection of the appropriately sized articular button 220, the practitioner inserts the pegs 253 on the anterior surface of the articular button 220 into the fixation cavities 254 of the bone protector plate 250 to form the modular patella trial assembly 210. The practitioner replaces the newly formed modular patella trial assembly 210 into the trochlear groove of the femur or femoral component and assesses patellar tracking by performing a range of motion (ROM) test on the patient that includes oscillation of the tibia or tibial component about the femur or femoral component in the clockwise and counterclockwise directions. If properly formed and assembled and appropriately sized, the trial assembly 210 should track normally throughout the ROM without tendency for tilting or lateral subluxation.

If the trial assembly 210 does not properly track throughout the ROM, the process may be repeated. The patella is inverted, the patellar trial removed, and a different sized trial is selected. The practitioner then inserts the differently sized articular button 220 into the bone protector plate 250 to form the trial assembly 210. After replacement of the trial assembly 210 into the trochlear groove, another ROM test is performed. Once the trial assembly properly tracks throughout the ROM, the bone protector plate 250 is removed from contact with the resected surface of the patella. Finally, the practitioner selects a permanent patella implant corresponding to the width 257, length 258, and an overall thickness combining the thickness 229 of the articular button 220 and the thickness 259 of the bone protector plate 250 and inserts peg features on the permanent implant into the drilled holes on the resected patella.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for reconstructing a patella of a patient, the method comprising the steps of:
    contacting a patella with a first protrusion extending from a plate; and
    inserting a portion of an articular button into a resected surface of the patella such that a first projection extending from the articular button extends towards a portion of the plate without extending through the plate and a second projection extending from the articular button extends towards a portion of the plate without being inserted into the resected surface of the patella.

2. The method of claim 1, further comprising a step of boring a first cavity into the resected surface of the patella.

3. The method of claim 2, further comprising boring two additional cavities into the resected surface of the patella.

4. The method of claim 2, further comprising a step of clamping the patella.

5. The method of claim 1, further comprising a step of clamping the patella.

6. The method of claim 1, wherein the contacting step includes inserting the first protrusion into the patella.

7. The method of claim 1, further comprising contacting the patella with a second protrusion extending from the plate.

8. The method of claim 7, further comprising contacting the patella with a third protrusion extending from the plate, wherein the first, the second, and the third protrusions are equidistant from each other.

9. The method of claim 1, wherein the plate includes a hole therethrough.

10. A method for reconstructing a patella of a patient, the method comprising the steps of:
    contacting a patella with a first protrusion extending from a plate; and
    inserting a portion of an articular button into a resected surface of the patella by inserting a first projection extending from the articular button into the resected surface of the patella such that second and third projections extending from the articular button extend towards the plate without extending through the plate.

11. The method of claim 10, further comprising boring at least one cavity into the resected surface of the patella.

12. The method of claim 11, further comprising boring two additional cavities into the resected surface of the patella.

13. The method of claim 11, further comprising a step of clamping the patella.

14. The method of claim 10, further comprising a step of clamping the patella.

15. The method of claim 10, wherein the contacting step includes inserting the first protrusion into the patella.

16. The method of claim 10, further comprising contacting the patella with a second protrusion extending from the plate.

17. The method of claim 16, further comprising contacting the patella with a third protrusion extending from the plate, wherein the first, the second, and the third protrusions are equidistant from each other.

18. The method of claim 10, wherein the plate includes a hole therethrough.

19. The method of claim 10, wherein the articular button is asymmetric about at least one axis.

20. A method for reconstructing a patella of a patient, the method comprising the steps of:
    contacting a patella with a plurality of protrusions extending from a plate;

boring a plurality of cavities into a resected surface of the patella;

inserting a portion of an articular button into the resected surface of the patella by inserting a first projection extending from the articular button into the resected surface of the patella such that second and third projections extending from the articular button extend towards the plate without extending through the plate; and inserting pegs of a patella implant into the cavities.

\* \* \* \* \*